United States Patent [19]
McCarthy et al.

[11] Patent Number: 5,217,979
[45] Date of Patent: Jun. 8, 1993

[54] SUBSTITUTED ALKYL PIPERIDINES

[75] Inventors: James R. McCarthy, West Chester; Charlotte L. Barney; Marion W. Wannamaker, both of Cincinnati, all of Ohio

[73] Assignee: Merrell Dow Pharmaceuticals Inc., Cincinnati, Ohio

[21] Appl. No.: 852,354

[22] Filed: Mar. 17, 1992

Related U.S. Application Data

[63] Continuation of Ser. No. 557,091, Jul. 27, 1990, abandoned, which is a continuation-in-part of Ser. No. 412,037, Sep. 22, 1989, abandoned.

[51] Int. Cl.$^5$ .................. C07D 211/14; C07D 211/32; C07D 211/26; A01K 31/445
[52] U.S. Cl. .................................... 514/315; 546/246; 546/247; 546/248
[58] Field of Search ............... 514/315; 546/246, 247, 546/248

[56] References Cited

U.S. PATENT DOCUMENTS

| | | | |
|---|---|---|---|
| 2,580,411 | 1/1952 | Cusic | 260/561 |
| 3,185,678 | 5/1966 | Abood | 260/239 |
| 4,326,067 | 4/1982 | Fazio | 548/347 |
| 4,812,451 | 3/1989 | Shanklin et al. | 514/318 |
| 4,906,659 | 3/1990 | Harada et al. | 514/478 |
| 4,940,705 | 7/1990 | Boshagen et al. | 514/315 |

FOREIGN PATENT DOCUMENTS

| | | |
|---|---|---|
| 1145616 | 3/1963 | European Pat. Off. . |
| 0029618 | 6/1981 | European Pat. Off. . |
| 0235942 | 9/1981 | European Pat. Off. . |
| 0866193 | 2/1953 | Fed. Rep. of Germany . |
| 3011504 | 3/1980 | Fed. Rep. of Germany . |
| 1261160 | 4/1961 | France . |
| 2272643 | 12/1975 | France . |
| 0505251 | 2/1969 | Switzerland . |
| 1415682 | 11/1975 | United Kingdom . |
| 1420758 | 1/1976 | United Kingdom . |

OTHER PUBLICATIONS

Chemical Abstracts 104(6):43107y, 1986 and 11th Collective Index, p51177cs 1-piperidinepentamide N-butyl-.

Chemical Abstracts 51(17):12097g, 1957, Terent'ev, et al., "Synthesis with acrylonitrile. III. Some 1-substituted pyrrolidines and piperidines".

Barney, et al., "A Convenient Synthesis of Hindered Amines and α-Trifluoromethylamines from Ketones," Tetrahedron Letters 31(39) pp. 5547–5550, 1990.

E. I. Mercer et al., Differences In The Inhibitory Effects of N-(1-n-Dodecyl)-Heterocycles on the 2,3-Oxzidosqualene Lanosterol-Cyclase of Rat Liver and Yeast, Comp. Biochem. Physiol., 80B(2), 341–346 (1985).

E. Jeney, et al., Molluscacidal Activities Of Organic Bases And Their Salts, Zentralbl. Bakteriol., Parasitenk., Infektionskr. Hyg., Abt. 1 Orig., 202(4), 539–46 (1967). Chemical Abstract 67(5):21035p Provided.

J. Berger, et al., Polyfunctionalized N-Surfactants, J. Prakt. Chem., 320(3), 433–51 (1978). Chemical Abstract 89(23):196901z Provided.

I. W. Mathison, et al., New Compounds, N,N-Dimethyl-[3-(1-alkylpiperidyl)]-carbamats, Potential Cholinesterase Inhibitors, J. Pharm. Sci. Pharm., 62(1), 158–60 (1973). Chemical Abstract 78(11)71860b Provided.

H. Matsuda, et al., Plant Growth Regulators Containing Amino Compounds, Japan Kokai Tokkyo Koho JP 63 02,904A2 (Jan. 7, 1988), Application No. 86/144409 filed Jun. 20, 1986. Chemical Abstract 109(7):50259f Provided.

Primary Examiner—John M. Ford
Attorney, Agent, or Firm—Michael J. Sayles

[57] ABSTRACT

The present invention relates to a group of compounds which are novel substituted alkyl piperidines and which act to inhibit the synthesis of cholesterol in mammals and in fungi.

23 Claims, No Drawings

SUBSTITUTED ALKYL PIPERIDINES

This is a continuation of application Ser. No. 07/557,091, filed Jul. 27, 1990, now abandoned, which is a continuation-in-part of application Ser. No. 07/412,037, filed Sep. 22, 1989, now abandoned.

FIELD OF THE INVENTION

The present invention relates to a group of compounds which are novel substituted alkyl piperidines and which act to inhibit the synthesis of cholesterol in mammals and in fungi.

BACKGROUND OF THE INVENTION

Vascular disease, because of its effects upon the heart, kidneys, extremities, and other vital organs, is a leading cause of morbidity and mortality in the United States and in most Western countries. In this regard, much has been learned about arteriosclerosis, atherosclerosis, and the lipidemias, with particular reference to cholesterol. In particular, there is convincing evidence of a reciprocal relationship between a high serum cholesterol and the incidence of atherosclerosis and its complications. Much interest has been expressed in recent years in reducing the level of serum cholesterol. However, some studies have shown that even radical reductions in dietary cholesterol achieves only a modest decrease of 10 to 15% in plasma cholesterol. Thus, it has been appreciated that further reductions in serum cholesterol will require other therapeutic measures, including the physiological inhibition of cholesterol synthesis in the body.

The enzymatic biosynthesis of cholesterol is a complex process, which requires altogether some 25 reaction steps. The pathway can be divided into three stages: (1) the conversion of acetic acid to mevalonic acid; (2) the conversion of mevalonic acid into squalene; and (3) the conversion of squalene into cholesterol. In the last stage of cholesterol biosynthesis, squalene is converted to squalene 2,3-epoxide via oxidation, a reaction catalyzed by squalene monooxygenase, also known as squalene epoxidase. The squalene 2,3-epoxide then undergoes cyclization to lanosterol, the first sterol to be formed.

The cyclization of 2,3-oxidosqualene to lanosterol is a key reaction in the biosynthesis of cholesterol in animals. The reaction is catalyzed by the microsomal enzyme 2,3-oxidosqualene lanosterol-cyclase. (See generally, Taylor, Frederick R., Kandutsch, Andrew A., Gayen, Apurba K., Nelson, James A., Nelson, Sharon S., Phirwa, Seloka, and Spencer, Thomas A., 24,25-*Epoxysterol Metabolism in Cultured Mammalian Cells and Repression of 3-Hydroxy-3-methylglutaryl-CoA Reductase, The Journal of Biological Chemistry*, 261, 15039-15044 (1986), incorporated herein by reference.)

In addition, it has recently been reported that certain compounds, such as allylamines, act as potent inhibitors of fungal squalene epoxidase. Fungal infections (mycoses) are found throughout the world. Only a few structural classes of compounds currently satisfy the demands of modern chemotherapy in their treatment and the search for new types of active substances is of major therapeutic importance. (See generally, Stutz, Anton, *allylamine Derivatives-A New Class of Active Substances in Antifungal Chemotherapy, Angew. Chem. Int. Ed. Engl.*, 26, 320–328 (1987).) As inhibitors of squalene epoxidase in animals, the compounds of the present invention are believed to be useful in the treatment of fungal infections through the inhibition of cholesterol synthesis.

SUMMARY OF THE INVENTION

The present invention relates to compounds having the following general formula:

FORMULA A and the pharmaceutically acceptable salts thereof wherein Y is —A—(Alk$_1$)—D—(Alk$_2$)—E—(Alk$_3$)—CH$_3$ wherein, A is —CH$_2$-,

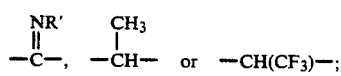

D and E are each independently

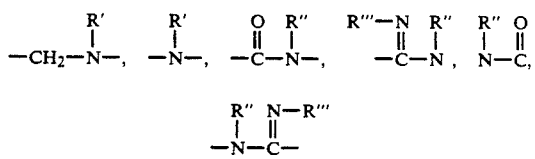

or a direct bond, with the proviso that when D is a moiety from the group E

E cannot be a moiety from the same group, and that when D is a moiety from the group

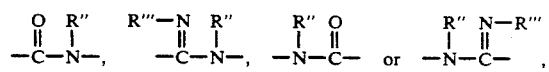

E cannot be a moiety from the same group;

(Alk$_1$), (Alk$_2$) and (Alk$_3$) are each independently a straight chain alkylene moiety containing from 0 to 5 carbon atoms, optionally substituted with up to 3 methyl groups, with the proviso that Alk$_2$ cannot have the value of 0 carbon atoms; or, (Alk$_1$), (Alk$_2$) and (Alk$_3$) are each independently a straight chain alkenylene moiety containing from 2 to 6 carbon atoms, the straight chain alkenyl moiety having 1 to 2 double bonds, and optionally substituted with up to 3 methyl groups;

R$_1$ is hydrogen, hydroxy or C$_{1-4}$ lower alkyl; and

R', R" and R'" are each independently hydrogen or C$_{1-4}$ lower alkyl.

As used in this application:

(a) the term alkylene refers to methylene, ethylene, propylene, butylene, pentylene and hexylene;

(b) the term alkenylene refers to any of the above alkylenes having 1 or 2 double bonds along the chain thereof; and, (c) the term C$_{1-4}$ lower alkyl refers to methyl, ethyl, propyl, isopropyl, butyl, sec-butyl and tertbutyl.

Also, as used in this application, the substituent represented as R$_1$ may be at any position from 2-6 around the piperidine ring. There may be up to three such independent substitutions around the piperidine ring wherein the substituent is other than hydrogen.

DETAILED DESCRIPTION OF THE INVENTION

In general, compounds of the present invention are prepared by the following methods.

REACTION SCHEME I

Compounds according to Formula A wherein D is

A is —CH$_2$— or

Alk$_3$ is an alkylene moiety of 0 carbon atoms, Alk$_1$ and Alk$_2$ and R" are defined as in Formula A, and E is a direct bond can be made according to the following reaction scheme, to form a product according to Formula I.

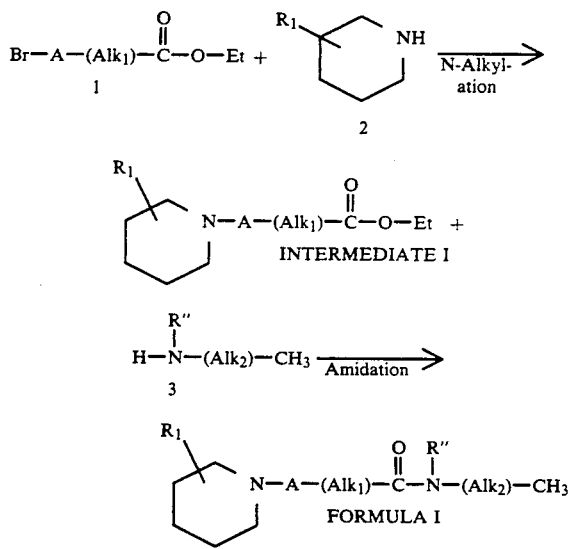

The first step in the reaction is the N-alkylation of piperidine by a bromoalkyl ester compound represented by structure 1. It will be understood that the abbreviation Br in this example and as used throughout this application represents bromine; however, the chloroalkyl ester may also be utilized. Likewise, it will be understood that the abbreviation Et in this example and as used throughout this application represents ethyl; however, other alkyl esters such as the methyl, propyl or isopropyl esters, for example, may also be utilized. The piperidine can be optionally substituted by R$_1$, as defined above and as represented by structure 2.

The appropriate starting compounds are a bromoalkyl ester wherein A and Alk$_1$ have the same definitions as that desired in the final product and a piperidine wherein R$_1$ has the same definition as desired in the final product, as represented by Formula I.

The alkylation reaction can be performed by techniques well known in the art. Typically the bromoalkyl ester 1 and the piperidine 2 are mixed in approximately a 1:2 molar ratio in a solvent, such as benzene, and the reaction mixture is heated at reflux under a nitrogen atmosphere, for example, for approximately 16 hours. Intermediate I is then recovered from the reaction mixture and purified by techniques known in the art. For example, the reaction mixture is concentrated under reduced pressure and then taken up in ether and filtered to give Intermediate I as shown.

The next step in the reaction scheme is an amidation reaction between Intermediate I and a substituted amine as shown in structure 3. The substituted amine chosen is one in which R" and Alk$_2$ have the same definition as R" and Alk$_2$ in the final product, represented by Formula I. The substituted amine and Intermediate I are contacted in approximately a 2:1 molar ratio in the presence of 2-hydroxypyridine and heated at approximately 60° C. for approximately 72 hours. The solution is poured into water, extracted with ethyl acetate, dried over magnesium sulfate and concentrated under reduced pressure. The final product is further purified using chromatographic techniques well known in the art such as flash chromatography.

REACTION SCHEME II

An amide according to Formula I, as prepared and defined above, can be reduced to the corresponding amine, wherein D is

and A, is —CH2— or

E is a direct bond and (Alk$_3$) is an alkylene moiety of-0 carbon atoms, Alk$_1$, Alk$_2$, R$_1$ and R' are defined as in Formula A, by mixing the amide with a reducing agent, such as lithium aluminum hydride, in an aprotic solvent, such as tetrahydrofuran (THF), to form a compound according to Formula II.

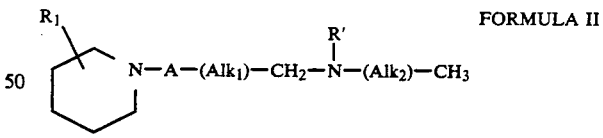

The amide made by the method of Reaction Scheme I is dissolved in THF. The solution is cooled to about 10° C. and a reducing agent, such as lithium aluminum hydride solution, is added dropwise. The reaction is stirred overnight at room temperature, for example, followed by heating the reaction to reflux.

The solution is then cooled to room temperature, quenched with water, dried over a drying agent such as magnesium sulfate and concentrated under reduced pressure. The resulting oil can be purified by techniques well known in the art. The resulting oil can be dissolved in ether, filtered and treated with anhydrous hydrochloric acid. The resulting precipitate is filtered and recrystallized in ethyl acetate/isopropyl alcohol, for example, to give the final product according to Formula II.

REACTION SCHEME III

Alternatively, the amide according to Formula I, as prepared and defined above, can be converted to the corresponding amidine, wherein D is

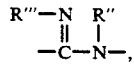

by first reacting the amide of Formula I with triethyloxonium tetrafluoroborate followed by addition of an amine of the structure R'''-NH$_2$ to form an amidine according to Formula III.

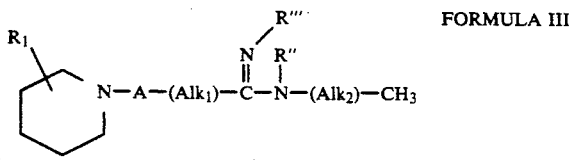
FORMULA III

The amine is chosen such that R''' has the same definition as the definition of R''' desired in the final product, as represented by Formula III.

An amide prepared according Reaction Scheme I is dissolved in methylene chloride and treated with approximately an equimolar amount of triethyloxonium tetrafluoroborate followed by an excess amount of the desired substituted amine. The reaction is stirred overnight at room temperature followed by heating the reaction to reflux.

The solution is then cooled to room temperature, quenched with water, dried over a drying agent such as magnesium sulfate and concentrated under reduced pressure. The resulting oil can be purified by techniques well known in the art. The resulting oil can be dissolved in ether, filtered and treated with anhydrous hydrochloric acid. The resulting precipitate is filtered and recrystallized in ethyl acetate/isopropyl alcohol, for example, to give the final product according to Formula III.

REACTION SCHEME IV

Amidines according to Formula IV can be prepared by the following reaction scheme. Formula IV is a representation of Formula A wherein D is

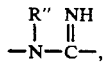

A is —CH$_2$—, or

Alk$_3$ is an alkyl moiety of 0 carbon, E is a direct bond and Alk1, Alk2, R$_1$ and R'' are defined as in Formula A.

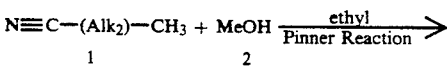

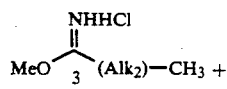

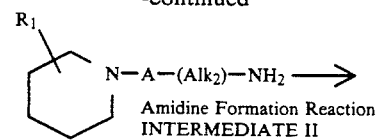

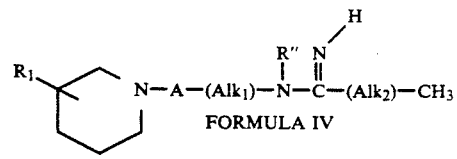
FORMULA IV

The first step in the reaction sequence is to conduct a Pinner reaction converting alkylnitrile 1, wherein Alk$_2$ has the same definition as that desired in the final product, to the imidate ester 3. The alkylnitrile 1 and an appropriate alcohol such as methanol 2 are mixed in approximately equimolar amounts in a solvent, such as ethyl ether and cooled to 0° C., then saturated with hydrochloric acid and stirred overnight at room temperature. The imidate ester 3 is concentrated under reduced pressure and can be purified by standard techniques such as trituration in ether, filtration and air drying. The resulting salt is taken up in ether, treated with cold saturated sodium bicarbonate, the layers separated and the aqueous washed with ether. The combined organics are dried, filtered and concentrated under reduced pressure to give the purified intermediate product 3.

The imidate ester 3 is then mixed with an appropriate N-substituted alkylamine piperidine represented by Intermediate II in a amidine formation reaction.

Intermediate II can be made as follows:

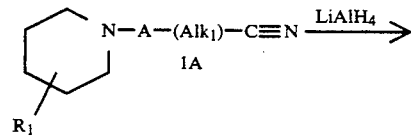

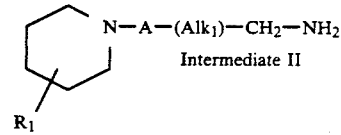

The alkylcyano piperidine 1A is chosen such that A and Alk$_1$ have the same definition as that desired in the final product. The alkylcyano piperidine 1A is mixed, dropwise, with an approximately equimolar amount of lithium aluminum hydride (LiAlH$_4$) powder in tetrahydrofuran. The reaction is heated at room temperature overnight, quenched with water and sodium hydroxide, filtered, washed and dried over magnesium sulfate, and concentrated under reduced pressure to give Intermediate II.

Intermediate II and the imidate ester are mixed in approximately equimolar amounts and allowed to stand overnight at room temperature.

The final product according to Formula V can be purified by standard techniques, i.e. the resulting oil is taken up in ether, filtered or treated with anhydrous hydrochloric acid, treated with sodium hydroxide, extracted with ether, drying over magnesium sulfate and concentrated under reduced pressure. The resulting oil can be dissolved in ether, filtered and treated with anhydrous hydrochloric acid. The resulting precipitate is filtered and recrystallized in ethyl acetate/isopropyl alcohol, for example, to give the final product according to Formula IV.

REACTION SCHEME V

The above amidine according to Formula IV, as prepared and defined above, can be hydrolyzed by treatment with hydrochloric acid to form an amide according to Formula V, wherein D is

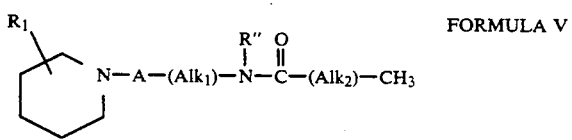

FORMULA V

The final product of Formula V as its hydrochloric acid salt can be collected by filtration and air dried.

REACTION SCHEME VI

The amide of Formula V, as prepared and defined above, can be treated with an alkylating agent, such as triethyloxonium tetrafluoroborate, followed by introduction of an excess amount of a substituted amine $H_2NR'''$ to form a substituted amidine according to Formula VI, wherein D is

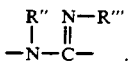

The amine $H_2NR'''$ is the chosen so that $R'''$ has the same definition as that desired in the final product.

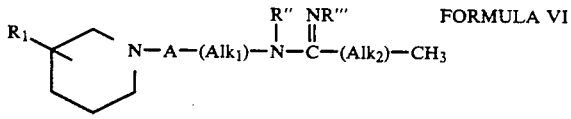

FORMULA VI

The final product according to Formula VI can be purified according to techniques well-known in the art. The resulting oil can be dissolved in ether, filtered and treated with anhydrous hydrochloric acid. The resulting precipitate is filtered and recrystallized in ethyl acetate/isopropyl alcohol, for example, to give the final product according to Formula VI.

In addition, complex compounds in which the alkyl side chain can include both an amine and an amide, or an amine and an amidine or an amide and an amidine can be prepared by the following reaction schemes.

REACTION SCHEME VII

Compounds according to Formula VII, wherein A is $-CH_2-$ or

D is

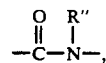

E is

and $Alk_1$, $Alk_2$, $Alk_3$, $R''$, $R'$ and $R_1$ are defined as in Formula A, can be made according to Reaction Scheme VII.

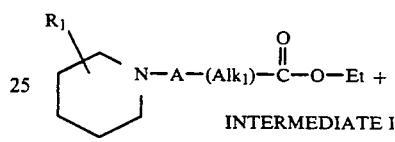

INTERMEDIATE I

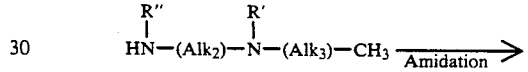

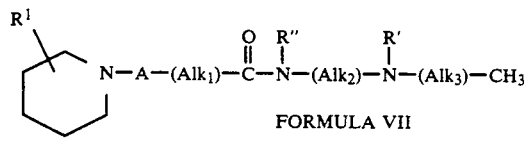

FORMULA VII

Intermediate I is prepared as described in detail above in Reaction Scheme I. Intermediate I is then contacted with the diamino alkyl 1 in approximately a 1:2 molar ratio in the presence of 2-hydroxypyridine. The diamino alkyl compound 2 is chosen so that the definition of $R'$, $R''$, $Alk_2$ and $Alk_3$ have the same definition as desired in the final product as represented by Formula VII. The reactants are then heated to approximately 60° C.

The resulting compound according to Formula VII can be extracted and purified according to methods known in the art. The resulting oil can be dissolved in ether, filtered and treated with anhydrous hydrochloric acid. The resulting precipitate is filtered and recrystallized in ethyl acetate/isopropyl alcohol, for example, to give the final product according to Formula VII.

REACTION SCHEME VIII

Further treatment of a compound according to Formula VII, as prepared and defined above, with an alkylating agent, such as triethyloxonium tetrafluoroborate, followed by the introduction of an excess amount of a substituted amine $H_2NR'$ results in a compound according to Formula VIII below, wherein D is

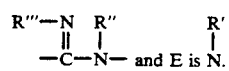 and E is N.

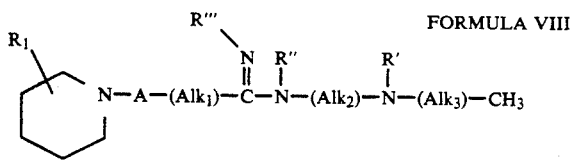

FORMULA VIII

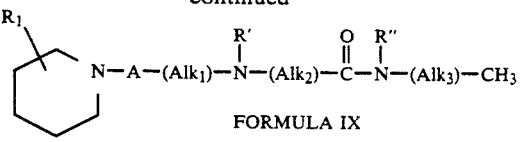

-continued

FORMULA IX

The amine H₂MR''' is chosen so that R''' had the same definition as the definition of R''' desired in the final product. An amide prepared according Reaction Scheme VII is dissolved in methylene chloride and treated with approximately an equimolar amount of triethyloxonium tetrafluoroborate followed by an excess amount of the desired substituted amine. The final product according to Formula III can be purified by techniques well-known in the art. The resulting oil can be dissolved in ether, filtered and treated with anhydrous hydrochloric acid. The resulting precipitate is filtered and recrystallized in ethyl acetate/isopropyl alcohol, for example, to give the final product according to Formula VIII.

REACTION SCHEME IX

Compounds according to Formula IX, wherein A is —CH₂— or

D is

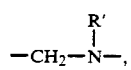

E is

and Alk₁, Alk₂, Alk₃, R', R'' and R₁ are defined as in Formula A, can be prepared by the following method.

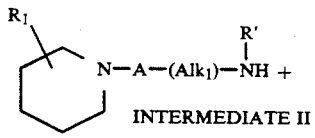

INTERMEDIATE II

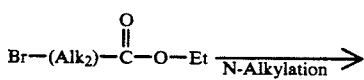

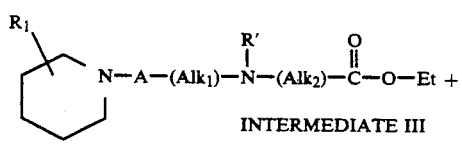

INTERMEDIATE III

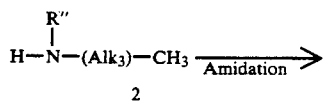

The first step in Reaction Scheme IX is the N-alkylation of the N-substituted piperidine represented by Intermediate II (from Reaction Scheme IV) by the bromoalkyl ester 1. The appropriate starting materials are a bromoalkyl ester in which Alk₂ has the same definition as that desired in the final product and a substituted piperidine in which R', A and Alk₁ have the same definitions as desired in the final product.

The alkylation reaction can be conducted utilizing techniques well known in the art. Typically the bromoalkyl ester 1 and the substituted piperidine Intermediate II are mixed in approximately a 1:2 molar ratio in a solvent, such as benzene, and the reaction mixture is heated at reflux under a nitrogen atmosphere, for example, for approximately 16 hours. Intermediate III is then recovered from the reaction mixture and purified by techniques known in the art. For example, the reaction mixture is concentrated under reduced pressure and then taken up in either and filtered to give the Intermediate III as shown.

The next step in the reaction scheme is an amidation reaction between Intermediate III and a substituted amine as shown in structure 2. The substituted amine chosen is one in which R'' and Alk₃ have the same definition as R'' and Alk₃ in the final product, represented by Formula IX. The substituted amine and Intermediate III are contacted in approximately a 2:1 molar ratio in the presence of 2-hydroxypyridine and heated at 60° C. for approximately 72 hours. The solution is poured into water, extracted with ethyl acetate, dried over magnesium sulfate and concentrated under reduced pressure. The final product is further purified using chromatographic techniques well known in the art such as flash chromatography.

REACTION SCHEME X

A compound according to Formula IX, as prepared and defined above, can be converted to the corresponding amidine by reacting it with triethyloxonium tetrafluoroborate, followed by an amine of the structure R'''—NH₂ to form a compound according to Formula X, wherein E is

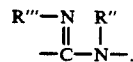

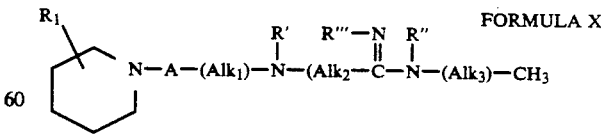

FORMULA X

The amine is chosen so that R''' has the same definition as the definition of R''' desired in the final product. An amide prepared according Reaction Scheme IX is dissolved in methylene chloride and treated with an approximately equimolar amount of triethyloxonium tetrafluoroborate, followed by an excess amount of the desired substituted amine. The final product according to Formula X can be purified by techniques well-known in the art as described in further detail in Reaction Scheme IX above.

Similarly, other complex compounds according to the invention can be made by the following methods.

REACTION SCHEME XI

Compounds according to Formula XI, wherein A is

or —$CH_2$—, D is

E is

$Alk_1$, $Alk_2$, $Alk_3$, R', R" and $R_1$ are defined as in Formula A, can be made by following the procedure of Reaction Scheme XI.

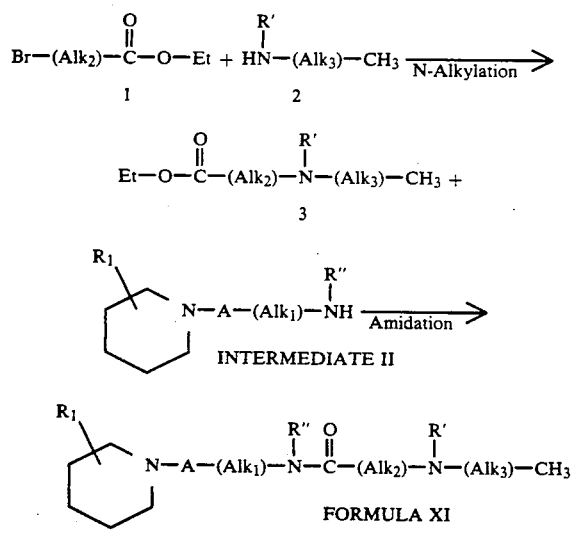

The first step in the reaction sequence is the N-alkylation of an appropriately substituted amine 2 by bromoalkyl ester 1. The appropriate starting materials are a bromoalkyl ester in which $Alk_2$ has the same definition as that desired in the final product and a substituted alkyl amine in which R' and $Alk_3$ have the same definitions as that desired in the final product. The alkylation reaction can be performed by techniques well known in the art. Typically the bromoalkyl ester 1 and the substituted amine 2 are mixed in approximately a 1:2 molar ratio in a solvent, such as benzene, and the reaction mixture is heated at reflux under a nitrogen atmosphere, for example, for approximately 16 hours. The alkylamine ester 3 is then recovered from the reaction mixture and purified by techniques known in the art. For example, the reaction mixture is concentrated under reduced pressure and then taken up in ether and filtered to give the alkylamine ester 3 as shown.

The next step in the reaction scheme is an amidation reaction between the alkylamine ester 3 and Intermediate II. The Intermediate II (from Reaction Scheme IV) chosen is one in which R" and $Alk_1$ have the same definition as $R_1$, R" and $Alk_1$ in the final product, represented by Formula XI. Intermediate II and the alkylamine ester 3 are contacted in approximately a 2:1 molar ratio in the presence of 2-hydroxypyridine and heated at 60° C. for approximately 72 hours, to yield a compound according to Formula XI.

The final product can then be extracted and purified according to methods well-known in the art. The solution is poured into water, extracted with ethyl acetate, dried over magnesium sulfate and concentrated under reduced pressure. The final product is further purified using chromatographic techniques well known in the art such as flash chromatography.

REACTION SCHEME XII

A compound according to Formula XI, as prepared and defined above, can be reacted with an amine of the structure $H_2NR'''$ to form a compound according to Formula XII, wherein D is $$\begin{array}{cc} R'' & N-R''' \\ | & \| \\ -N- & C- \end{array}$$

and E is $$\begin{array}{c} R' \\ | \\ -N-. \end{array}$$

FORMULA XII

The amine is chosen so that R''' has the same definition as that desired in the final product. An amide prepared according Reaction Scheme XI is dissolved in methylene chloride and treated with approximately an equimolar amount of triethyloxonium tetrafluoroborate followed by an excess amount of the desired substituted amine. The reaction is stirred overnight at room temperature followed by heating the reaction to reflux. The solution is then cooled to room temperature, quenched with water, dried over a drying agent such as magnesium sulfate and concentrated under reduced pressure.

The resulting oil can be purified by techniques well known in the art. The resulting oil can be dissolved in ether, filtered and treated with anhydrous hydrochloric acid. The resulting precipitate is filtered and recrystallized in ethyl acetate/isopropyl alcohol, for example, to give the final product according to Formula XII.

Compounds according to Formulas XIII and XIV can be made by the following reaction schemes.

REACTION SCHEME XIII

A mixed amine of amide according to Formula XIII, wherein A is —$CH_2$— or

D is 

E is 

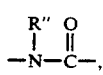,

Alk₁, Alk₂, Alk₃, R', R" and R₁ are defined as in Formula A can be made by the following method.

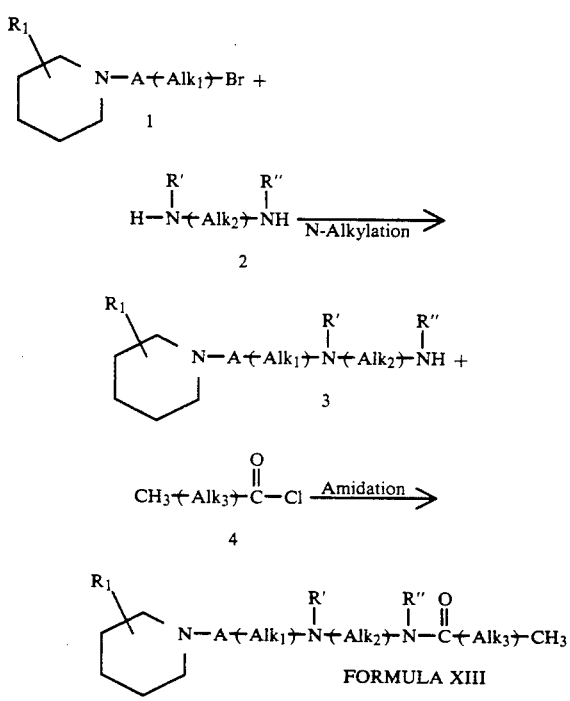

FORMULA XIII

The first step in the reaction is the N-alkylation of the alkylbromo piperidine 1 by a diamino alkyl 1. The alkylbromo piperidine 1 and the diamino alkyl 2 are chosen so that $R_1$, A, $Alk_1$, R', R" and $Alk_2$ have the same definitions as desired in the final product. The reactions are mixed in approximately a 1:2 molar ratio in a solvent, such as benzene, and the reaction mixture is heated at reflux under a nitrogen atmosphere, for example, for approximately 16 hours. The resulting product 3 is then recovered from the reaction mixture and purified by techniques known in the art. For example, the reaction mixture is concentrated under reduced pressure and then taken up in either and filtered to give the product 3 as shown.

The second step of the reaction scheme is to conduct an amidation reaction. The product 3 is reacted with the acid chloride 4, in which $Alk_3$ has the same definition as the definition of $Alk_3$ desired in the final product, and one equivalent of triethylamine. The reactants are mixed in approximately equimolar amounts in methylene chloride at 0°–10° C. under inert atmosphere.

The resulting oil can be purified by techniques well known in the art. The resulting oil can by dissolved in ether, filtered and treated with anhydrous hydrochloric acid. The resulting precipitate is filtered and recrystallized in ethyl acetate/isopropyl alcohol, for example, to give the final product according to Formula XIII.

REACTION SCHEME XIV

A compound according to Formula XIII, as defined above, can be reacted with an amine of the structure H₂NR'" to form a compound according to Formula XIV, wherein A is —CH₂— or D is 

and E is

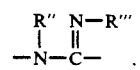.

The amine H₂NR'" is chosen so that R'" has the same definition as that desired in the final product as represented by Formula XIV.

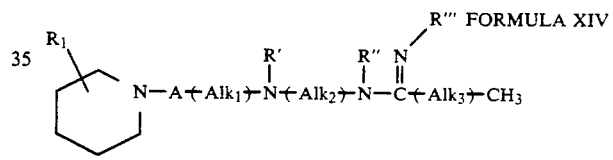

FORMULA XIV

An amide prepared according Reaction Scheme XIII is dissolved in methylene chloride and treated with an approximately equimolar amount of triethyloxonium tetrafluoroborate followed by an excess amount of the desired substituted amine. The reaction is stirred overnight at room temperature followed by heating the reaction to reflux.

The solution is then cooled to room temperature, quenched with water, dried over a drying agent such as magnesium sulfate and concentrated under reduced pressure. The resulting oil can be purified by techniques well known in the art. The resulting oil can be dissolved in ether, filtered and treated with anhydrous hydrochloric acid. The resulting precipitate is filtered and recrystallized in ethyl acetate/isopropyl alcohol, for example, to give the final product according to Formula XIV.

REACTION SCHEME XV

Compounds according to Formula XV can be prepared according to the following reaction scheme. In this example, A is

, both D and E represent direct bonds and therefore Alk₁, Alk₂ and Alk₃ are represented by $Alk_x$, in which x is an integer from 1 to 18.

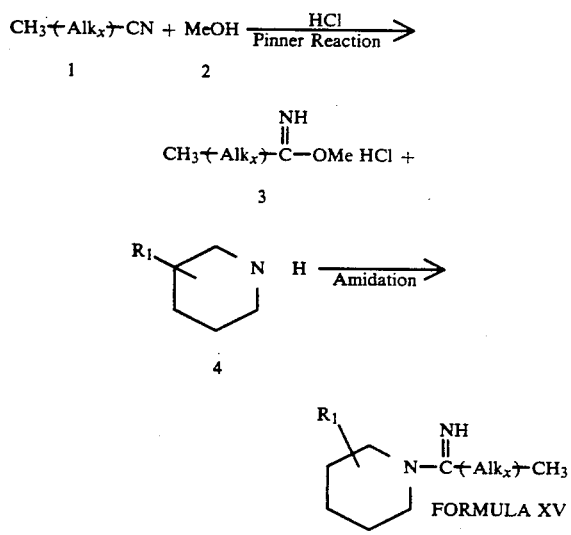

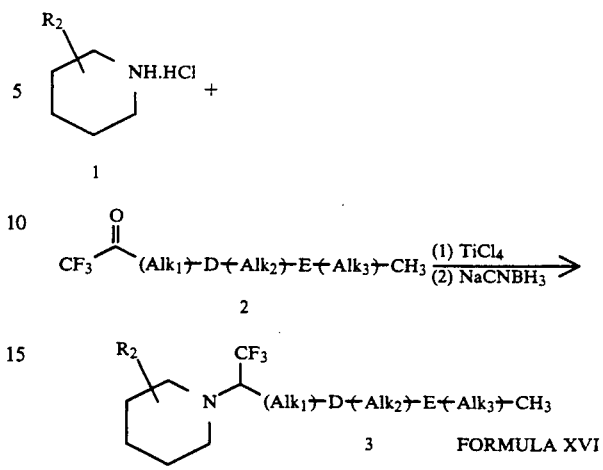

The first step in the reaction sequence is to conduct a Pinner reaction between an alkyl cyanide 1 and an appropriate alcohol such as methanol 2. The appropriate starting material is an alkyl cyanide 1 in which $Alk_x$ has the same definition as that desired in the final product.

The Pinner reaction can be conducted utilizing techniques well-known in the art. Typically, approximately equimolar amounts of alkyl cyanide 1 and an appropriate alcohol 2 are contacted in a solvent such as ether. The reagents are mixed and cooled to about 0° C., followed by the introduction of an acid, such as hydrochloric acid, until saturation. The reaction mixture is stirred overnight.

The imidate ester 3 produced via the above reaction can be recovered from the reaction mixture and purified by techniques well-known in the art. For example, the resulting precipitate is concentrated under reduced pressure, triturated with ether, filtered and air dried to give the imidate ester 3.

The above acid salt is then taken up in ether, treated with ice-cold sodium bicarbonate, the layers separated, the aqueous extracted with ether and the combined organics dried over magnesium sulfate and concentrated under reduced pressure.

The second step of the reaction scheme is to conduct an amidation reaction. The above product is mixed with an approximately equimolar amount of piperidine in methanol and allowed to stand at room temperature overnight.

The final product can be recovered and purified by techniques well-known in the art. For example, the reaction is concentrated under reduced pressure, triturated with ether and the resulting solid product collected by vacuum filtration, washed with ether and air-dried to give the final product according to Formula XV.

REACTION SCHEME XVI

Compounds according to Formula XVI can be made by the following method. Formula XVI is a representation of Formula A wherein A is —CH(CF$_3$)—, and R$_1$, R', R'', R''', D, E, (Alk$_1$), (Alk$_2$), and (Alk$_3$) are all defined as above in Formula A.

First, the appropriately substituted piperidine hydrochloride 1 is reacted with a trifluoromethyl ketone, such as depicted by 2. The trifluoromethyl ketone 2 is prepared as shown in Reaction Scheme XVIA below.

REACTION SCHEME XVIA

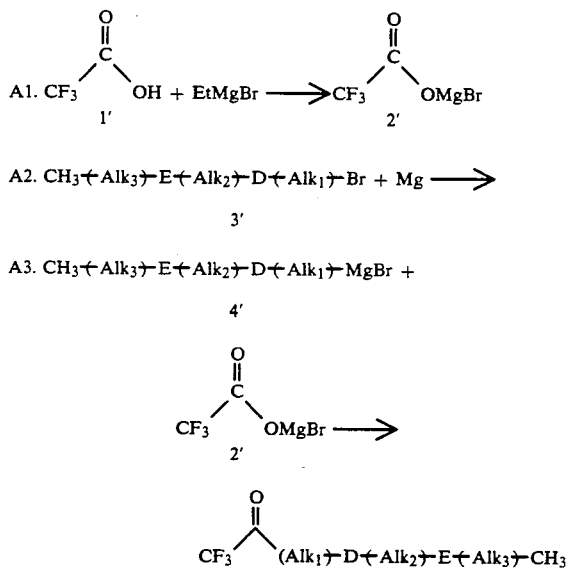

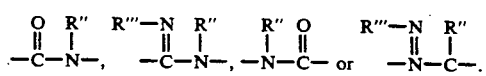

In Reaction Scheme XVIA, (Alk$_1$), (Alk$_2$), (Alk$_3$), D and E are defined as above in Formula A, with the proviso that D or E is not $$\begin{matrix} O & R'' & R'''-N & R'' & R'' & O & R'''-N & R'' \\ \| & | & \| & | & | & \| & \| & | \\ -C-N-, & -C-N-, & -N-C- & \text{or} & -N-C-. \end{matrix}$$

First, magnesium bromide trifluoroacetate 2' is prepared according to Reaction Scheme XVIA1. To a solution of trifluoroacetic acid 1' dissolved in an appropriate organic solvent, such as anhydrous ether, is added an approximately equimolar amount of a Grignard reagent, such as ethylmagnesium bromide (EtMgBr), in solution in anhydrous ether at low temperature (−5° C.) under a nitrogen atmosphere. The reaction is then allowed to warm to room temperature.

Next, the desired alkylmagnesium bromide 4' is prepared according to Reaction Scheme XVIA2. The appropriate alkylbromide 3' is chosen such that ($Alk_1$), ($Alk_2$), ($Alk_3$), D and E are all defined the same as that desired in the product 4'. The alkylbromide 3' is either known in the art or is prepared by methods generally known in the art. The alkylbromide 3' in solution with anhydrous ether is added to magnesium in anhydrous ether (equimolar amounts of alkylbromide 3' and magnesium). The reaction is stirred at room temperature until the magnesium is dissolved.

To the flask containing the magnesium bromide trifluoroacetate 2' is added the alkylmagnesium bromide 4', in approximately equimolar amounts, at low temperature ($-5°$ C.) under a nitrogen atmosphere. The reaction is stirred for about 1 hour at room temperature, refluxed for several hours, cooled to about $0°$ C. and then hydrolyzed by the dropwise addition of 5N hydrochloric acid, for example. The layers are then separated, the aqueous extracted with ethyl acetate, the combined organic extracts are washed with cold saturated sodium bicarbonate, and dried. Evaporation yields an oil which can be purified by distillation to yield the trifluoromethylalkyl ketone 3 according to Reaction Scheme XVIA.

Referring now to Reaction Scheme XVI, the trifluoromethylalkyl ketone 2 and the substituted piperidine hydrochloride 1 are then mixed in approximately equimolar amounts in the presence of an excess of triethylamine and anhydrous methylene chloride at about $10°$ C. under nitrogen atmosphere. Titanium tetrachloride is added dropwise over about 10 minutes in a molar amount approximately half that of the molar amount of the trifluoromethylalkyl ketone 2. The reaction is stirred at room temperature for approximately 48 hours, then carefully quenched with a methanolic solution of excess sodium cyanoborohydride. The reaction is made acidic with 5N hydrochloric acid, then made basic with 5N sodium hydroxide, for example. The desired product is extracted with ethyl acetate, dried over magnesium sulfate and evaporated, providing the trifluoromethylalkyl substituted piperidine 3.

As examples of compounds of the present invention are the following:
1. N-(3-Methylbutyl)-1-piperidine propanamide hydrochloride.
2. 4-(3-Methylbutylamino)-1-piperidinobutane dihydrochloride.
3. N-(3-Piperidinopropyl)-4-methylvalerylamidine.
4. N-Butyl-N-methyl-1-piperidinebutyramide.
5. N-(4-Piperidinobutyl)-4-methylvalerylamidine.
6. Piperidine octylamidine hydrochloride.
7. N-(1-trifluoromethyl-undecane)-piperidine.

The following assays are used to test compounds for their ability to inhibit 2,3-oxidosqualene lanosterol-cyclase or epoxidase. Microsomes, prepared by ultracentrifugation of homogenates of rat liver, are incubated at $37°$ C. for 45 minutes in the presence of 60 $\mu$M 3H-squalene, 2.0 mM NADPH, 0.01 mM FAD, and the high speed supernatant fraction from the microsomal preparation. Blanks, in which NADPH has been omitted, are run simultaneously with the test compounds. Compounds are tested at concentrations of $>0.0$ to 100.0 $\mu$M.

Method 1

Following incubation the samples are saponified, standards are added to each sample, and then the reaction products are extracted into hexane. The hexane extracts are dried and then the dried extracts are redissolved in chloroform. The reaction products contained in the extracts are then separated by thin layer chromatography (TLC). Spots containing the reaction products are scraped from the TLC plates and counted for radioactivity in a scintillation counter. An $IC_{50}$ is finally calculated.

Method 2

Following incubation reactions are stopped by the addition of chloroform:methanol, standards are added, then reaction products and standards are extracted into chloroform. The chloroform extracts are dried, and the residue is dissolved in toluene:methanol. The reaction products and standards contained in the dissolved residue are separated by high performance liquid chromatography (HPLC). Chromatographic peaks containing reaction products are monitored for radioactivity with a flow-through scintillation counter connected in series with the HPLC column. An $IC_{50}$ is calculated based on the radioactivity in controls and samples.

Pharmaceutical Preparations of the 2,3-Oxidosqualene Lanosterol-Cyclase Inhibitors The compounds of this invention are useful both in the free base form and in the form of acid addition salts. The acid addition salts are simply a more convenient form for use and, in practice, use of the salt amounts to use of the free base. The expression "pharmaceutically acceptable acid addition salts" is intended to apply to any non-toxic organic or inorganic acid addition salts of the base compounds of the above compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the sulfonic acids such as p-toluenesulfonic, methanesulfonic acid and 2-hydroxyethanesulfonic acid. Either the mono- or the di-acid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the anesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The exact amount of the compound or compounds to be employed, i.e., the amount of the subject compound or compounds sufficient to provide the desired effect, depends on various factors such as the compound employed; type of administration; the size, age and species of animal; the route, time and frequency of administration; and, the physiological effect desired. In particular cases, the amount to be administered can be ascertained by conventional range finding techniques.

The compounds are preferably administered in the form of a composition comprising the compound in admixture with a pharmaceutically acceptable carrier, i.e., a carrier which is chemically inert to the active compound and which has no detrimental side effects or toxicity under the conditions of use. Such compositions can contain from about 0.1 $\mu$g or less to 500 mg of the active compound per ml of carrier to about 99% by weight of the active compound in combination with a pharmaceutically-acceptable carrier.

The compounds may also be incorporated into any inert carrier so that they may be utilized in routine serum assays, blood levels, urine levels, etc., according to techniques well known in the art.

The compositions can be in solid forms, such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as *Remington's Pharmaceutical Manufacturing*, 13 Ed., Mack Publishing Co., Easton, Pennsylvania (1965).

The following examples are presented to illustrated the present invention but they should not be construed as limiting in any way.

EXAMPLE 1

Ethyl 4-bromobutyroate (10.0 g, 0.513 mmol) and 9.37 g (0.110 mmol) of piperidine were mixed in benzene (25 ml) and heated at reflux under nitrogen atmosphere overnight.

The reaction was concentrated under reduced pressure, taken up into ether and filtered. The filtrate was shaken with saturated sodium bicarbonate, the layers separated, the aqueous layer extracted with ethyl ether (2×50 ml). The combined organics were dried over magnesium sulfate and concentrated under reduced pressure to give 8.68 g of a yellow oil (85%).

Next, 4.0 g (0.02 mmol) of the above product was mixed with 4.4 g (0.05 mmol) isopentylamine in the presence of 1.4 g (0.015 mmol) 2-hydroxypyridine and heated together at 60° C. in a closed tube (screw cap) and followed by gas chromatography. After 72 hours, the solution was poured into 200 ml water, extracted with ethyl acetate (3×75 ml), dried over magnesium sulfate and concentrated under reduced pressure to give 4.21 g of an orange oil (50% yield). Flash chromatography (methylene chloride followed by 10% methanol/methylene chloride) gave 3.1 g of an orange oil.

The above product (2.08 mmol) was dissolved in ether and treated with gaseous hydrochloric acid to give a pale orange solid. Recrystallization (ethyl acetate/isopropyl alcohol) gave 296 mg of a white crystal product N-(3-methylbutyl)-1-piperidine propanamide hydrochloride (m.p. 77°–82° C.). Anal. Calcd. for $C_{14}H_{28}N_2O$ HCl 1.3 $H_2O$: C, 56.00; H, 10.61; N, 9.53; Found: C, 56.17; H, 10.28; N, 9.36.

EXAMPLE 2

The above product (1.0 g, 0.00416 mmol) was dissolved in tetrahydrofuran (25 ml) in an oven-dried, 3-necked, 100 ml round-bottomed flask, equipped with a stir bar, thermometer, $N_2$-line and addition funnel (rubber septum). This was cooled to 10° C. and 5 ml (1.0M in ethyl ether, 0.005 mmol) lithium aluminum hydride (LAH) added dropwise. The reaction was stirred overnight at room temperature then heated at reflux. An additional 5 ml LAH solution was added and the reaction continued at reflux. The solution was cooled to room temperature, quenched with 400 ml of water, dried over magnesium sulfate and concentrated under reduced pressure to give 740 mg of a low melting, oily solid (79%). The oil was dissolved in ether, filtered and treated with anhydrous hydrochloric acid. The resulting precipitate was filtered, recrystallized (ethyl acetate/isopropyl alcohol) to give a white solid, m.p. 261°–264° C. 4-(3-methylbutylamino)-1-piperidinobutane dihydrochloride. Anal. Calcd. for $C_{14}H_{30}N_2$ 2HCl $H_2O$: C, 52.99,; H, 10.80; N, 8.83. Found: C, 53.34; H, 10.82; N, 8.93.

EXAMPLE 3

4-Methylvaleronitrile (10.0 g, 0.103 mmol) and 100 ml of ethyl ether were mixed in 3.5 g (0.110 mmol) methanol and cooled to 0° C., then saturated with hydrochloric acid and stirred overnight at room temperature.

The reaction, which contained a small amount of white precipitate, was concentrated under reduced pressure, triturated with ether, filtered and air dried to give 10.5 g of a white fluffy solid, m.p. 105°–105.5° C.

Next, 1.0 g of the above hydrochloric acid salt was taken up in ether, treated with cold saturated sodium bicarbonate, the layers separated, the aqueous washed with ether (2×10 ml), the combined organics dried, filtered and concentrated under reduced pressure to give 470 mg of a clear oil (60.3%).

The above product (9.5 g, 0.0573 mmol) was mixed with 8.16 g (0.0573 mmol) of 3-piperidino-1-propylamine and
to stand overnight at room temperature ($CaCl_2$ tube). The reaction was concentrated under reduced pressure to give 16.5 g of an orange oil. The oil was redissolved in 50 ml methanol, treated with decolorizing carbon, filtered and concentrated under reduced pressure to give 15.4 g of a yellow oil. The oil was treated with saturated sodium bicarbonate, then 5N sodium hydroxide, extracted 3 times with ethyl acetate, dried over magnesium sulfate/potassium carbonate and concentrated under reduced pressure to give 6.0 g of a clear oil, which was taken up in anhydrous ether, filtered and treated with anhydrous hydrochloric acid. It was then treated with 5N sodium hydroxide, extracted with ether (3×50 ml), dried over magnesium sulfate/potassium carbonate and concentrated under reduced pressure to give 4.8 g of N-(3-piperidinopropyl)-4-methylvalerylamidine as a clear oil.

EXAMPLE 4

First, 10.0 g (0.05 mmol) of ethyl 4-bromobutyrate and 9.37 g (0.110 mmol) of piperidine were mixed in 50 ml of benzene in a 100 ml, 1-necked, round-bottomed flask and heated at reflux under $N_2$-atmosphere overnight.

The reaction, which contained a white precipitate, was treated with saturated sodium bicarbonate, the layers separated, the aqueous layer washed with ethyl acetate (2×30 ml), the combined organics dried over magnesium sulfate and concentrated under reduced pressure to give 8.57 g of a yellow oil (83.8%).

Next, 2.4 ml (20 mmol) of N-methylbutylamine and 50 ml of anhydrous methylene chloride were placed in an oven-dried, 3-necked 100 ml round-bottomed flask equipped with a stir bar, thermometer, addition funnel (rubber septum), and $N_2$-line. Trimethylaluminum (10 ml, 20 mmol, 2.0M in toluene) was added dropwise at room temperature and the reaction stirred for 15 min. The above oil (4.0 g, 20 mmol) in 15 ml anhydrous methylene chloride was added dropwise and the reaction monitored by gas chromatography.

The reaction was carefully quenched with 1N HCl, basified with 5N sodium hydroxide, the layers separated, the aqueous extracted with methylene chloride (2×50 ml), dried over magnesium sulfate and concentrated under reduced pressure to give 4.12 g of product (86% yield). Flash chromatography (methylene chloride, then 10% methanol/methylene chloride) gave 1.95 g of a yellow, low melting solid, N-butyl-N-methyl-1-piperidinebutyramide.

EXAMPLE 5

Lithium aluminum hydride (2.5 g, 0.068 mmol, powder) was placed in an oven-dried, 3-necked, round-bottomed flask equipped with a stir bar, thermometer, addition funnel (rubber septum) and $N_2$-line. Tetrahydrofuran (THF) (50 ml) was added, followed by dropwise addition of 4-(N-piperidino)-butyronitrile (10.0 g, 0.0658 mmol) in 50 ml of THF.

The reaction was heated at room temperature overnight. The solution was quenched by the careful addition of 2.5 ml of water, 2.5 ml of sodium hydroxide, an additional 9 ml of water, filtered, washed with brine, dried over magnesium sulfate and concentrated under reduced pressure to give 7.7 g of an orange oil.

Next, 4-methylvaleronitrile (10.0 g, 0.103 mmol) was dissolved in ether, treated with methanol (3.5 g, 0.111 mmol) and cooled to 0° C. Anhydrous hydrochloric acid was introduced until saturation and the reaction stirred at room temperature under $N_2$-atmosphere overnight.

The orange-pink reaction was concentrated under reduced pressure, triturated with ether and the resulting off-white solid collected by vacuum filtration and air-dried to give 4.3 g of product.

Next, methyl 4-methylvalerylimidate (2.12 g, 0.0128 mmol) and 4-piperidino-1-butylamine (2.0 g, 0.0128 mmol) were mixed in 25 ml anhydrous methanol and stirred overnight under nitrogen atmosphere.

The reaction was treated with 5N sodium hydroxide, extracted with ether (3×25 ml), dried over magnesium sulfate/potassium carbonate and then concentrated under reduced pressure to give 1.0 g of N-(4-piperidinobutyl)-4-methylvalerylamidine as a yellow oil.

EXAMPLE 6

Octyl cyanide (10.0 g, 0.0718 mmol) and 50 ml ethyl ether were mixed in 2.56 g (0.08 mmol) methanol and cooled to 0° C., then saturated with hydrochloric acid and allowed to stir overnight.

The reaction, which contained a small amount of precipitate, was concentrated under reduced pressure, triturated with ether, filtered and air dried to give 9.44 g of a white fluffy solid (63.6%), m.p. 90°-92° C.

The above product, methyl octylimidate hydrochloride (8.44 g, 0.0406 mmol), was mixed with 3.5 g (0.0406 mmol) piperidine in 50 ml methanol and allowed to stand at room temperature overnight (CaCl₂ tube). The reaction was concentrated under reduced pressure, triturated with ether and the resulting white solid collected by vacuum filtration and washed with ether, then air-dried to give 8.54 g of a white oily solid (85.2%).

Recrystallization with ethyl acetate gave 3.4 g of piperidine octylamidine hydrochloride as white crystals (m.p. 123°-125° C). High resolution mass spectroscopy calculated for $C_{13}H_{20}N_2$: 210.2096. Found: 210.2087.

EXAMPLE 7

Preparation of N-(1Trifluoromethyl-Undecane)-Piperidine
Preparation of Magnesium Bromide Trifluoroacetate (1)

To a dry flask containing trifluoroacetic acid (15 g, 0.132 mmol) and anhydrous ether (50 ml) was added a solution of ethylmagnesium bromide (66 ml of a 2 M solution in tetrahydrofuran, 0.132 mmol) in anhydrous ether (50 ml) at −5° C. under nitrogen atmosphere. The reaction was allowed to warm to room temperature.

Preparation of Decanylmagnesium Bromide (2)

To a dry flask containing magnesium (2.64 g, 0.11 mmol) and anhydrous ether (50 ml) was added a solution of 1-bromodecane (24.3 g, 0.11 mmol) in anhydrous ether (50 ml) under nitrogen atmosphere. The reaction was stirred at room temperature until the magnesium had dissolved.

Preparation of Trifluoromethyl-2-Dodecanone (3)

To the flask containing magnesium bromide trifluoroacetate (1) was added the solution of decanylmagnesium bromide (2) at −5° C. under nitrogen atmosphere. The reaction was stirred for 1 hour at room temperature, refluxed for 12 hours, cooled to 0° C. and hydrolyzed with the dropwise addition of 5N hydrochloric acid (50 ml). The layers were separated, the aqueous extracted with ethyl acetate (2×20 ml), the combined organics washed with cold saturated sodium bicarbonate, then brine, and dried over magnesium sulfate. Evaporation gave 14.1 g of yellow oil which was purified by distillation providing trifluoromethyl-2-dodecanone (3) as a clear oil (10.1 g, 38%), b.p. 125° C. @ 0.1 mm Hg. ¹H-NMR (300 MHz, CDCl₃) δ 0.85 (3H, t), 1.30 (14H, br s), 1.65 (2H, m), 2.70 (2H, t); ¹⁹F—NMR (CDCl₃) δ −80.02 (s); MS (CI/CH₄) 239 (M+H), 169 (M+H−HCF₃).

Preparation of N-(1-Trifluoromethyl-Undecane)-Piperidine (4)

To a dry flask containing trifluoromethyl-2-dodecanone (3) (4.0 g, 16.8 mmol), piperidine hydrochloride (1.84 g, 15.1 mmol), triethylamine (5 g, 50.4 mmol), and anhydrous methylene chloride (80 ml) at 10° C. under nitrogen atmosphere was added titanium tetrachloride (8.4 ml of a 1 M solution in methylene chloride, 8.4 mmol) dropwise over 10 minutes. The reaction was stirred at room temperature for 48 hours, then carefully quenched with a methanolic solution of sodium cyanoborohydride (3.4 g, 50.4 mmol in 20 ml methanol). The reaction was stirred for 1 hour, carefully taken to pH 1 with 5N hydrochloric acid, stirred for 30 minutes, then taken to pH 13 with 5N sodium hydroxide. The desired product was extracted with ethyl acetate (3×75 ml), dried over magnesium sulfate, and evaporated providing 4.5 g orange oil. The oil was dissolved in ether, filtered, and treated with anhydrous hydrochloric acid. The white solid was collected and recrystallized (ethyl acetate/isopropyl alcohol) providing N-(1-trifluoromethyl-undecane)-piperidine (4) as a white crystalline solid (740 mg); m.p. 124°-125° C., ¹H—NMR (300 MHz, DMSO-d₆, 90° C.) 80.85 (3H,t), 1.30 (14H, br s), 1.4–1.9 (10H, m), 2.5 (1H, m), 2.75 (1H, m), 2.95 (1H,m); ¹⁹F—NMR (DMSO-d₆, 120° C.) 8—67 (br s); MS (CI/CH₄) 308 (M+H), 306 (M−H), 288 (M+H−HF); High Resolution MS (FT) Anal. Calcd. for $C_{17}H_{32}F_3N$: 307.249. Found: 307.246.

What is claimed is:

1. A compound according to formula:

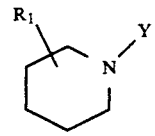

and the pharmaceutically acceptable salts thereof wherein Y is —A—(Alk₁)—D—(Alk₂)—E—(Alk₃)—CH₃ wherein, A is —CH₂—,

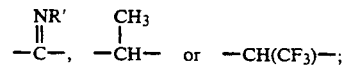

D and E are each independently

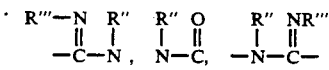

or a direct bond with the proviso that when D is a moiety from the group

E cannot be a moiety from the same group, and that when D is a moiety from the group

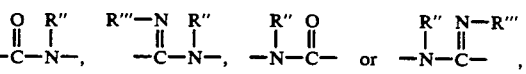

E cannot be a moiety from the same group;

(Alk₁); (Alk₂) and (Alk₃) are each independently a straight chain alkylene moiety containing from 0 to 5 carbon atoms, optionally substituted with up to 3 methyl groups, with the proviso that Alk₂ cannot have the value of 0 carbon atoms; or, (Alk₁), (Alk₂) and (Alk₃) are each independently a straight chain alkenylene moiety containing from 2 to 6 carbon atoms, the straight chain alkenylene moiety having 1 to 2 double bonds, and optionally substituted with up to 3 methyl groups;

$R_1$ is hydrogen, hydroxy or $C_{1-4}$ lower alkyl; and R', R" and R'" are each independently hydrogen or $C_{1-4}$ lower alkyl.

2. A compound according to claim 1 wherein A is —$CH_2$— or

D is

and E is

and the pharmaceutically acceptable salts thereof.

3. A compound according to claim 1 wherein A is —$CH_2$— or

D is

and E is

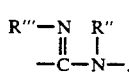

and the pharmaceutically acceptable salts thereof.

4. A compound according to claim 1 wherein A is —$CH_2$— or

D is

and E is

and the pharmaceutically acceptable salts thereof.

5. A compound according to claim 1 wherein A is —$CH_2$— or

D is

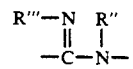

and E is

and the pharmaceutically acceptable salts thereof.

6. A compound according to claim 1 wherein A is —$CH_2$— or

D is

and E is

and the pharmaceutically acceptable salts thereof.

7. A compound according to claim 1 wherein A is —$CH_2$— or

D is

and E is

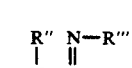

and the pharmaceutically acceptable salts thereof.

8. A compound according to claim 1 wherein A is —$CH_2$— or

D is

and E is

and the pharmaceutically acceptable salts thereof.

9. A compound according to claim 1 wherein A is —CH₂— or

D is

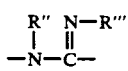

and E is

and the pharmaceutically acceptable salts thereof.

10. A compound according to claim 1 wherein A is

and D and E are direct bonds, and the pharmaceutically acceptable salts thereof.

11. A compound according to claim 1 wherein A is —CH₂— or

D is

and E is a direct bond, and the pharmaceutically acceptable salts thereof.

12. A compound according to claim 1 wherein A is —CH₂— or

D is

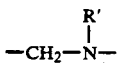

and E is a direct bond, and the pharmaceutically acceptable salts thereof.

13. A compound according to claim 1 wherein A is —CH₂— or

D is

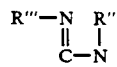

and E is a direct bond, and the pharmaceutically acceptable salts thereof.

14. A compound according to claim 1 wherein A is —CH₂— or

D is

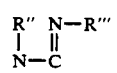

and E is a Direct bond, and the pharmaceutically acceptable salts thereof.

15. A compound according to claim 1 wherein A is —CH₂— or

D is

and E is a Direct bond, and the pharmaceutically acceptable salts thereof.

16. A compound according to claim 1 which is N-(3-methylbutyl)-1-piperidine propanamide, and the pharmaceutically acceptable salts thereof.

17. A compound according to claim 1 which is 4-(3-methylbutylamino)-1-piperidinobutane, and the pharmaceutically acceptable salts thereof.

18. A compound according to claim 1 which is N-(3-piperidinopropyl)-4-methylvalerylamidine, and the pharmaceutically acceptable salts thereof.

19. A compound according to claim 1 which is N-butyl-N-methyl-1-piperidinebutyramide, and the pharmaceutically acceptable salts thereof.

20. A compound according to claim 1 which is N-(4-piperidinobutyl)-4-methylvalerylamidine, and the pharmaceutically acceptable salts thereof.

21. A compound according to claim 1 which is piperidine octylamidine, and the pharmaceutically acceptable salts thereof.

22. A compound according to claim 1 which is N-(1-trifluoromethyl-undecane)-piperidine.

23. A pharmaceutical composition having a plasma cholesterol lowering effect comprising a compound of claim 1 in a therapeutically effective amount in admixture with a pharmaceutically acceptable carrier.

* * * * *